US012793309B2

(12) United States Patent
Zimmermann et al.

(10) Patent No.: US 12,793,309 B2
(45) Date of Patent: Nov. 10, 2026

(54) AVATAR APPARATUS AND METHOD FOR REPRESENTING A PERSON AND FOR PROCESSING PERSON-RELATED DATA OF THE PERSON

(71) Applicants: Fraunhofer-Gesellschaft zur Foerderung der angewandten Forschung e. V., Munich (DE); Universitaet des Saarlandes, Saarbruecken (DE)

(72) Inventors: Heiko Zimmermann, Sulzbach (DE); Andreas Kurtz, Berlin (DE); Antonie Fuhr, Berlin (DE)

(73) Assignee: Fraunhofer-Gesellschaft zur Foerderung der Angewandten Forschung e. V., Munich (DE)

( * ) Notice: Subject to any disclaimer, the term of this patent is extended or adjusted under 35 U.S.C. 154(b) by 649 days.

(21) Appl. No.: 18/039,647

(22) PCT Filed: Dec. 11, 2020

(86) PCT No.: PCT/EP2020/085821

§ 371 (c)(1),
(2) Date: May 31, 2023

(87) PCT Pub. No.: WO2022/122173

PCT Pub. Date: Jun. 16, 2022

(65) Prior Publication Data

US 2024/0005580 A1 Jan. 4, 2024

(51) Int. Cl.
*G06T 13/40* (2011.01)
*G06F 21/62* (2013.01)
(Continued)

(52) U.S. Cl.
CPC .......... *G06T 13/40* (2013.01); *G06F 21/6254* (2013.01); *G16H 10/20* (2018.01); *G16H 50/20* (2018.01)

(58) Field of Classification Search
None
See application file for complete search history.

(56) References Cited

U.S. PATENT DOCUMENTS

| | | | |
|---|---|---|---|
| 10,672,288 | B2 | 6/2020 | Ribeira et al. |
| 2015/0127593 | A1 | 5/2015 | Gramuglio et al. |

(Continued)

FOREIGN PATENT DOCUMENTS

| | | | |
|---|---|---|---|
| CN | 107111894 | A | 8/2017 |
| DE | 102019135380 | A1 | 6/2021 |

(Continued)

OTHER PUBLICATIONS

International Search Report for related PCT Application No. PCT/EP2020/085821 dated Aug. 4, 2021.

(Continued)

*Primary Examiner* — Samuel D Fereja
(74) *Attorney, Agent, or Firm* — Caesar Rivise, PC

(57) ABSTRACT

An avatar apparatus that is adapted to represent a person and to process personal data of the person comprises an AI processor device that is adapted for machine learning of individual mental response characteristics of the person by way of data training, wherein the AI processor device is configured to generate semantic answers in response to questions in a manner dependent on the mental response characteristics, a first storage device that is coupled to the AI processor device and is adapted to store the mental response characteristics of the person, an input device that is coupled to the AI processor device and is adapted to interact with the person and/or to receive questions relating to the person, and (Continued)

an output device that is configured to output signals that represent the answers generated by the AI processor device. An avatar system with multiple avatar apparatuses, uses of the avatar apparatus, and an avatar method for operating the avatar apparatus, are also described.

26 Claims, 2 Drawing Sheets

(51) Int. Cl.
*G16H 10/20* (2018.01)
*G16H 50/20* (2018.01)

(56) References Cited

U.S. PATENT DOCUMENTS

2018/0077088 A1 3/2018 Cabrera-Cordon et al.
2018/0165582 A1 6/2018 Cha
2019/0122093 A1 4/2019 Yonekura
2019/0354553 A1 11/2019 Eguchi et al.
2020/0227178 A1 7/2020 Lombardi et al.
2022/0245429 A1 8/2022 Zimmermann et al.
2022/0292331 A1 9/2022 Zimmermann et al.
2022/0384001 A1* 12/2022 Gnanasambandam ...................... G16H 10/20
2023/0015147 A1 1/2023 Wall Warner et al.
2023/0021229 A1 1/2023 Zimmermann et al.

FOREIGN PATENT DOCUMENTS

JP 2018011262 A 1/2018
JP 2018112814 A 7/2018
JP 2020149721 A 9/2020
WO WO2017217507 A1 12/2017
WO WO2020233850 A1 11/2020
WO WO2020233851 A1 11/2020

OTHER PUBLICATIONS

Office Action from corresponding Chinese Patent Application No. 202080107874.0 dated May 20, 2026.
Office Action from related Korea Patent Application No. 10-2023-7019778 dated Apr. 17, 2026.

* cited by examiner

AVATAR APPARATUS AND METHOD FOR REPRESENTING A PERSON AND FOR PROCESSING PERSON-RELATED DATA OF THE PERSON

CROSS-REFERENCE TO RELATED APPLICATIONS

This application is a U.S. National Phase Application under 35 U.S.C. § 371 of PCT/EP2020/085821, filed Dec. 11, 2020, the contents of which is incorporated herein by reference in its entirety.

BACKGROUND OF THE INVENTION

The present invention relates to an avatar apparatus ("ethical avatar") that is adapted to represent a person and to process person related data of the person, to an avatar system having multiple avatar apparatuses, to applications of the avatar apparatus, and to an avatar method for operating the avatar apparatus. The invention relates in particular to a method for developing, and a device for establishing, a virtual representative of a person, also referred to here as ethical avatar or as the avatar apparatus, wherein the avatar apparatus can for example learn and independently simulate individual moral attitudes, ethical principles, values and/or further opinions and interests of the persons. The invention may be used for example in the operation of databases with personal data of persons and/or in the processing of personal data, in particular by machine learning and/or artificial intelligence (AI).

Both in (bio)medical research and during the medical examination and treatment of persons (patients and/or subjects), a large amount of personal data relating to the patients or subjects is accumulated, be it through the donation of biological material (tissue samples, samples from somatic cells or stem cells) or in the course of the treatment of diseases (taking of biopsies, removal of tumours or the like). The personal data relate for example to the genetic information of the patient/subject, their disease history and/or any environmental influences to which they are exposed.

The administration and protection of such data require great expenditure on information technology, associated with the primacy of complying with ethical standards in the handling of this data (see the regulations for data protection and "informed consent").

Declarations of consent have hitherto been obtained from persons in writing, and anonymisation or pseudo-anonymisation of the identities of the patients/subjects has been used to protect sensitive data against unauthorised access by third parties. This necessary approach makes it very difficult or even impossible to survey the persons concerned at a later point in time. If situations change, new fields of research open up or there are uncertainties with regard to the opinion or the interests of the persons, it is no longer possible, or it is possible only with great difficulty, for the questions arising from this to be resolved by the persons concerned.

It is also the case in opinion research, in sociological or demographic analyses, in the course of Big Data studies (data science) and in the industrial/commercial sector that large amounts of personal data have to be processed as quickly as possible whilst safeguarding the privacy of the persons concerned; this has hitherto been very time-consuming and expensive.

In the field of personalised medicine, attempts are already being made to digitalise human body functions and body units (see for example the "Blue Brain Project" or virtual heart simulations). It is ever more common for digital versions of human body parts to be developed: it is sought to be able to virtually represent cells, organs or even entire individuals. This concept is referred to as "digital twinning"—a digital twin of the biological counterpart is generated.

Previous approaches have been limited to simulating physiological processes of the human. By contrast, mental response characteristics, such as moral attitudes, opinions, individual values and ethical principles of a person, have hitherto not been taken into consideration.

A method for establishing an AI device is described in WO 2020/233850 A1 (Recursive coupling of artificial learning units") and WO 2020/233851 A1 ("Coupling multiple artificially learning units with a projection level"), which introduce not only the establishment of a learning system consisting of several AI units but also the storage and independent application of ethical principles/rules by AI systems.

SUMMARY

It is the objective of the invention to provide an improved data-based digital representation of a person, and/or methods for the use thereof, whilst avoiding disadvantages of conventional techniques. The digital representation of a person is intended in particular to allow additional information, and/or information in extended categories, such as non-physiological information about the person, to be provided, and/or for enhanced uses to be offered. The digital representation of a person is furthermore intended in particular to provide faster and/or easier access to statements from the person, and/or to offer protection for the privacy of the person.

Said objective is achieved by means of an avatar apparatus, an avatar system with multiple avatar apparatuses, uses of the avatar apparatus, and an avatar method for operating the avatar apparatus, having the features of the independent claims. Advantageous embodiments and applications of the invention become apparent from the dependent claims.

According to a first general aspect of the invention, the above objective is achieved by means of an avatar apparatus that is adapted to represent a person and to process personal data of the person. The avatar apparatus comprises an AI processor device that is adapted for machine learning of individual mental response characteristics of the person by way of data training, wherein the AI processor device is configured to generate semantic answers (in particular at least one sentence or individual words, such as yes or no) in response to questions in a manner dependent on the mental response characteristics, a first storage device (personal storage) that is coupled to the AI processor device and is adapted to store the mental response characteristics of the person, an input device that is coupled to the AI processor device and is adapted to interact with the person and/or to receive questions relating to the person, and an output device that is configured to output signals that represent the answers generated by the AI processor device.

According to a second general aspect of the invention, the above objective is achieved by the use of the avatar apparatus according to the first general aspect of the invention or an embodiment thereof, wherein the use comprises at least one of the following: forming a multidirectional platform for placing medical laboratories and/or biobanks in connection with industrial companies and/or scientific research organisations, forming a platform for social research, opinion research and/or Big Data analysis, forming a platform for providing patient declarations, in particular declarations of consent to the use of personal data, forming a data protection platform, generating a patient decree of the person, providing input information for a synthetic biological procedure, and controlling technical systems.

According to a third general aspect of the invention, the above objective is achieved by an avatar method for operating the avatar apparatus of a person according to the first general aspect of the invention or an embodiment thereof, comprising the steps of receiving at least one question relating to the person, processing the question using the AI processor device, and outputting a semantic answer to the at least one question.

According to a fourth general aspect of the invention, the above objective is achieved by means of an avatar system that comprises multiple avatar apparatuses according to the first general aspect of the invention or an embodiment thereof, wherein each avatar apparatus is adapted to a different use.

With the avatar apparatus, the mental response characteristics of persons are advantageously digitalised and/or simulated by the AI processor device. The AI processor device comprises a computer device that is adapted to use a program based on machine learning, for example at least one artificial neural network. The expression “AI processor device” will hereinafter also be used to refer to the artificial intelligence provided by the computer device.

The avatar apparatus advantageously provides a digital twin of the person to which the avatar apparatus relates, wherein the avatar apparatus represents for example individual opinions, interests and/or moral attitudes of the real person. The avatar apparatus advantageously makes it possible to simplify and/or speed up the administration of the personal data. At the same time, the avatar apparatus makes it possible to protect the privacy of the person concerned and to take their interests into consideration to a maximum degree.

The avatar apparatus according to the invention advantageously constitutes an intelligent, digital and predictively usable aid that can act as a representative of real persons. The avatar apparatus is for example usable as an advisory link between persons, on the one hand, and enquiring entities, such as research organisations or institutions or companies, on the other hand, wherein the anonymity of the person concerned is safeguarded (direct contact with the person is no longer necessary), and at the same time, the interests of the person can be represented in dealings with others. These advantages are described below, in particular with reference to the figures.

The avatar apparatus is advantageously a tool that can predict statements, in particular opinions, of its real counterpart and can be used in all forms of databases/analyses where it has hitherto been necessary to survey thousands of persons in a time-consuming and expensive manner.

The ethical avatar constitutes an artificial intelligence (AI) that is capable of being trained by persons in particular with regard to their moral attitudes, and of subsequently anticipating answers to newly posed questions on the basis of this training. During this training, the AI of the avatar learns the moral attitudes, values, interests and principles of the person. Using a learning, associative AI, the avatar can then use said principles/values/attitudes when answering new (ethical) questions. The avatar apparatus is thus capable not only of expressing what it has learned but also of intelligently and creatively applying what it has learned in new contexts. It can intelligently predict, on the basis of its knowledge of the person concerned, what the opinions and judgements of said person would be in response to questions in a particular new context.

The AI processor device is preferably adapted for machine learning of the individual mental response characteristics, which include moral attitudes, opinions, values, interests and/or ethical principles of the person. The response characteristics comprise subjective characteristics of the person that characterise how the person responds to a question, a fact, an experience, a situation, another person, a social group and/or a concept, wherein responses may include for example the articulation of statements, emotions and/or forms of behaviour.

In a preferred embodiment of the invention, the first storage device is configured to store the mental response characteristics in the form of catalogues of rules, micro-contracts and/or blockchains. The implementation of the invention is however not restricted to these variants but is also possible with other digitalisable formats.

Preferably, the first storage device is adapted to store individual additional data on which the mental response characteristics are dependent and which include in particular a religious affiliation, a group affiliation, an association membership and/or a party membership of the person.

According to a further advantageous embodiment of the invention, the AI processor device is adapted to understand and use ethically relevant expressions.

A second storage device (public storage, shared storage) is preferably provided, which is adapted to store general additional data that represent knowledge relevant to the mental response characteristics. The second storage device is particularly preferably coupled to an update device by means of which the general additional data can be updated.

According to a further advantageous embodiment of the invention, the avatar apparatus, in particular the input device, has a communication channel that is adapted for communication between the avatar apparatus and the person. This advantageously makes it possible for the person to access the avatar apparatus, for example in order to check the functioning thereof, to train the AI processor device, or to modify stored data.

Therefore, not only is the avatar apparatus trained by the person concerned, but the real person, whose moral attitudes the avatar apparatus simulates, furthermore preferably has the capability, at any time, to monitor and if necessary correct the statements, in particular decisions, made by their ethical avatar, to train the latter further, or to make changes to the stored values/interests/moral principles. The person however also has the option to transfer the decision-making authority entirely to, and allow themselves to be represented entirely by, their avatar.

The autonomy of the real person is advantageously not restricted, because the avatar functions merely as an assistive representative which is under the control of the person at all times and which merely performs advisory functions on the basis of the mental response characteristics, such as individual opinions and interests, of the person.

According to a further advantageous variant of the invention, the input device is provided with an authorising device that is configured to restrict the receipt of questions relating to the person to predetermined authorised entities, such as pharmaceutical companies and/or research organisations, and/or to predetermined allowable contents. The authorising device particularly preferably comprises a communication authentication storage and a standard communication protocol function.

In this embodiment, the protection of the personal data of the person is of particular importance: the avatar does not allow unauthorised parties to access the data, and also, when answering questions that are posed to it, provides personal data only to a limited extent and only to authorised entities.

The avatar apparatus preferably furthermore comprises a cryptographic storage that is adapted to store access keys. It is thus advantageously made possible for access to the avatar apparatus to be restricted in a highly reliable manner.

According to a further advantageous embodiment of the invention, the avatar apparatus has a log storage that is adapted to store a course of changes to the contents of the first and/or second storage devices.

Furthermore, a timer device may advantageously be provided, which is adapted to provide a timescale for the functions of the avatar apparatus.

The avatar apparatus particularly preferably comprises a communication device that is adapted to establish contact, and/or to communicate, with the person. This advantageously makes it possible, for example, for the semantic answer provided by the AI processor device to be verified.

The features disclosed in conjunction with the avatar apparatus and its embodiments likewise constitute preferred features of the method according to the invention, and vice versa. The abovementioned aspects and inventive and preferred features, in particular relating to the establishment of the avatar apparatus and the functions and configurations of the individual components that are described in conjunction with the avatar apparatus, therefore also apply to the method. The preferred embodiments, variants and features of the invention described above are combinable with one another.

BRIEF DESCRIPTION OF THE DRAWINGS

Further details and benefits of the invention will be described below with reference to the appended drawings. The drawings schematically show.

DETAILED DESCRIPTION

Features of exemplary embodiments of the invention will be described below with reference to the configuration and functions of the avatar apparatus. Details of the AI processor device will not be described insofar as they are known from conventional techniques. An AI processor device may in particular be configured as described in WO 2020/233850 A1 ("Recursive coupling of artificial learning units") and WO 2020/233851 A1 ("Coupling multiple artificially learning units with a projection level"). WO 2020/233850 A1 and WO 2020/233851 A1 are incorporated by reference into the present disclosure, in particular with regard to the configuration of the AI processor device and its peripheral equipment, such as input and output devices and memories.

Figure 1:
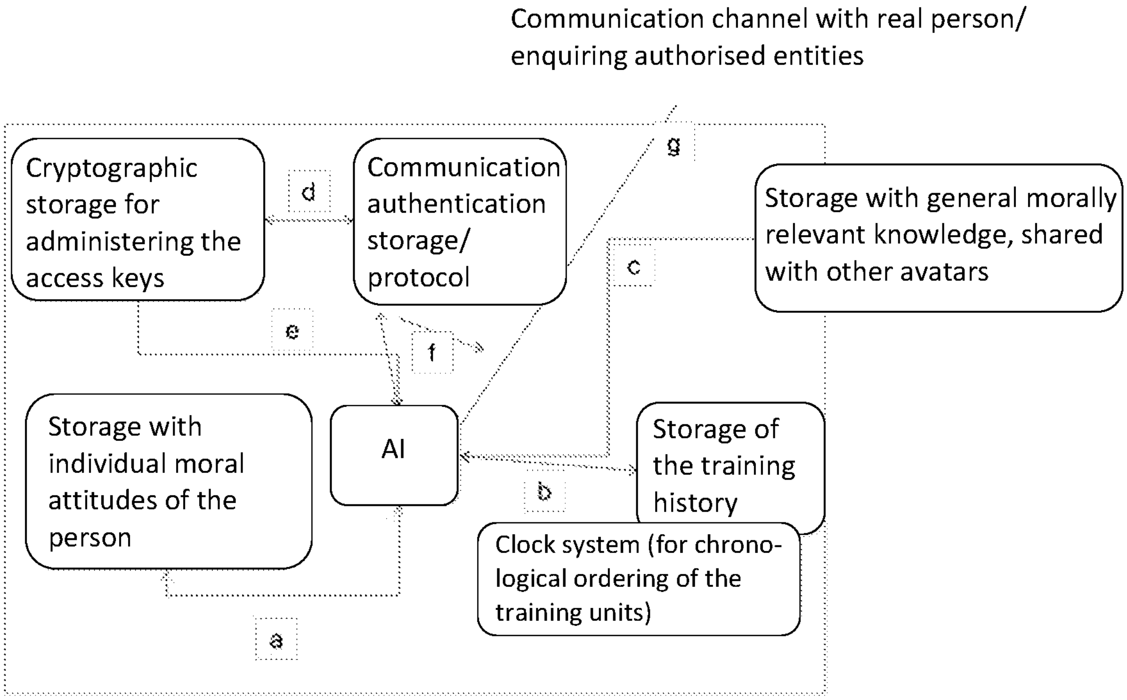
FIG. 1: an overview illustration of an avatar apparatus with features according to preferred embodiments of the invention.

FIG. 1 shows an embodiment of the avatar apparatus and the functioning thereof, wherein the sections (steps and/or components) a to g shown in FIG. 1 have the following meanings. Section a comprises storing the material that has been learned and/or accessing the material that has been learned, section b comprises logging the times of the training units, section c comprises accessing the second storage device in order to be able to make a survey more intelligent and compare same with a timer device (clock system), section d comprises an interaction between key administration and authentication storage, section e involves defining who is authorised to ask questions and/or receive information, section f comprises influencing the enablement or prevention of communication with the surroundings, in particular a communication protocol, and section g relates to a channel for the AI to be trained by a person, for the AI to be surveyed, and/or for the AI to provide information.

Figure 2:
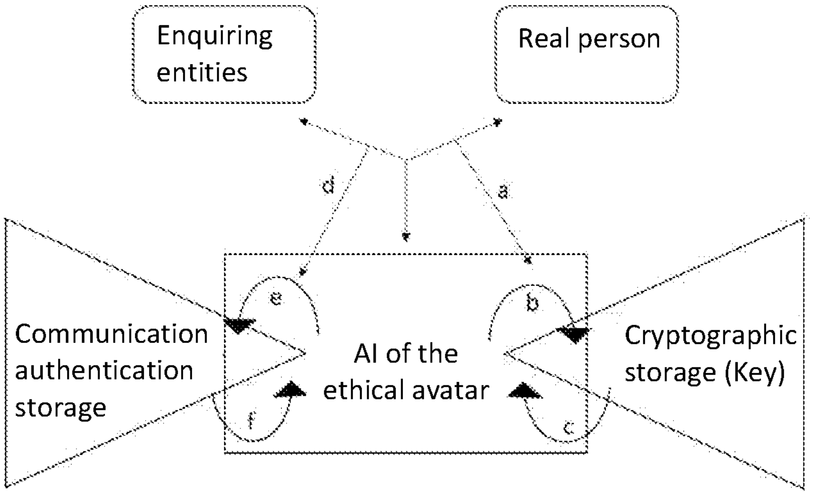
FIG. 2: an illustration of the communication, and of the monitoring of the communication, between the avatar apparatus and its surroundings (outside world)
Figure 4:
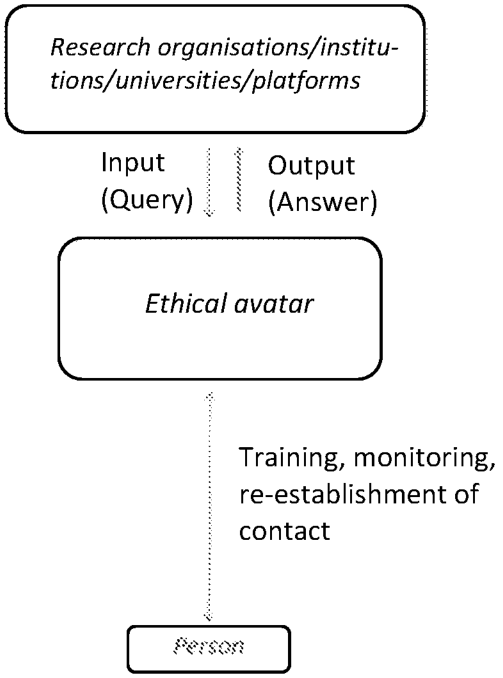
FIG. 4: an overview illustration of an avatar method with features according to preferred embodiments of the invention.

The communication (see FIG. 4) and monitoring of the communication between the avatar apparatus and its surroundings (outside world, in particular enquiring entities or the real person training the avatar) comprises the following steps, as per FIG. 2. Step a is a communication with the real person. In step b, the AI processor device uses its cryptographic storage to verify whether the person is authorised to make changes in, and/or to communicate with, the personal storage. In step c, yes/no decisions are made as to whether to allow training and/or yes/no decisions are made as to whether to provide information. Step d is a received query relating to a particular topic from an entity such as a research organisation. In step e, the AI processor device of the avatar uses a directory of all authorised entities in its communication authentication storage to check whether said AI processor device is authorised to provide information to said entity and on what topics said AI processor device is authorised to provide information to said entity, wherein, in particular, of a protocol of the communication in the communication authentication storage is used. In step f, the result of the check is provided.

Figure 3:
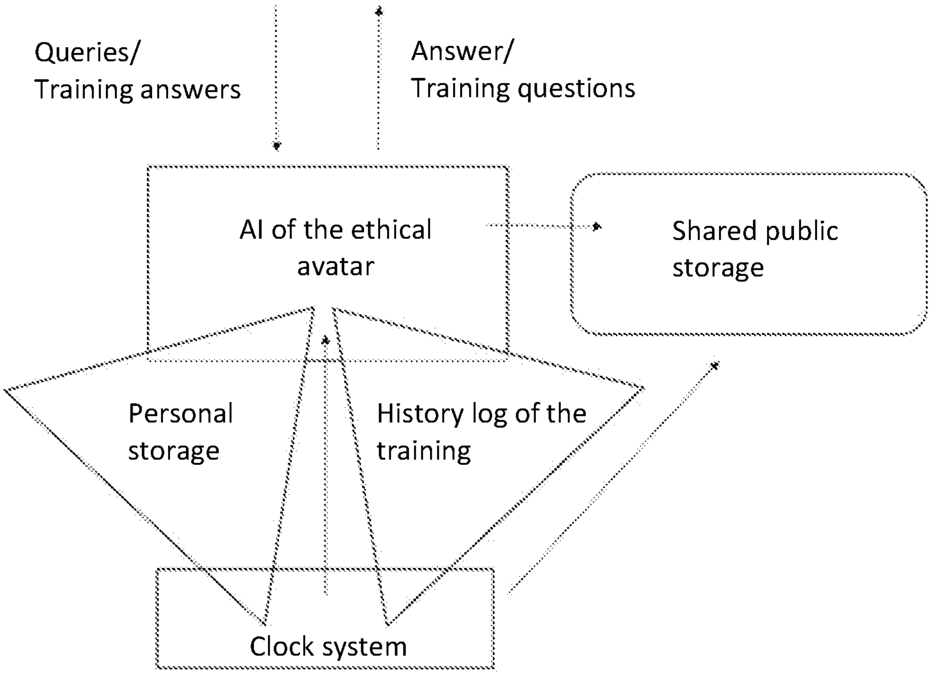
FIG. 3: an illustration of the use of the first and second storage devices.

FIG. 3 illustrates the storage of data and the retrieval of data at the first storage device (personal storage) in combination with the use of the second storage device (shared public storage) for the purposes of chronologically ordering the training contents. The AI processor device of the ethical avatar is not only capable of storing the present mental response characteristics, for example moral attitudes/opinions/interests, of a real person in a personal storage and of accessing same (in the event of authorised queries, see FIG. 2) but can also store older versions of the mental response characteristics of the real person in a history log and place them in absolute chronological order using a clock system. This chronological assignment also allows alignment with the second storage device. The second storage device can furthermore use the AI processor device to make the training by the real person more intelligent, for example by virtue of the AI processor device asking for the religious denomination of the person and understanding the response "Christian" by accessing the second storage device, because it has been recorded in said second storage device what "being Christian" means with regard to the moral attitudes at a particular point in time.

The avatar apparatus has the following characteristics, illustrated in FIG. 1:

- the avatar apparatus comprises (1) a learning component which, through personal training by real persons, can learn their moral attitudes, wherein
- (2) the results of this training are stored in the first storage device, and the AI of the avatar can access this information (the first storage device is not public, that is to say access from the surroundings of the avatar apparatus is blocked). The mental response characteristics, such as moral beliefs, of the person may be stored in the form of catalogues of rules, micro-contracts and/or blockchains in the first storage device of the avatar. Information relating to religious affiliation or group/association/party memberships of the person may be stored in the first storage device, and from these the ethical avatar is capable of drawing conclusions regarding the opinions of the person (by accessing a separate storage (second storage device, see (4)).

Furthermore, (3) the avatar apparatus is adapted to independently generate new answers (output) to new questions (input) on the basis of its stored knowledge relating to the mental response characteristics, for example attitudes, of the person. Such an avatar is preferably capable of understanding and using ethically relevant expressions, which is made possible by way of corresponding ontology (in particular systematic, formalised representation of entities, such as physical and abstract subjects, characteristics, facts, events, methods).

Aside from the first storage device for the moral attitudes of the person, the avatar (4) can preferably access a separate, second storage device, in which more fundamental knowledge that is relevant for the response characteristics, for example morally relevant knowledge, is stored (from prior professional training). This may for example be knowledge relating to various ethical theories and their implications, relating to religions or other groups (such as parties or associations) and their codes and rules, or else knowledge relating to ethically relevant expressions and ethical dilemma situations that are known and discussed in moral philosophy. Said second storage device (public storage, which is for example shared with other avatar systems) could be used by the avatar apparatus, during its training by persons, in order to survey the person more intelligently, to sensitise the person to particular questions, and to be able to categorise the answers from the person. The avatar uses this general knowledge only during the training, but not when answering ethical questions on behalf of its person at a later point in time. In this case, the avatar makes decisions only in relation to what it knows regarding the mental response characteristics, in particular individual values/interests/principles, of said person. The second storage device may be updated at regular intervals, for which purpose a clock system within the avatar (see (9)) is used.

(5), a communication channel is provided between the ethical avatar and its real counterpart, the person, such that said person can train the avatar and can, preferably at all times, monitor the behaviour of its digital representative and/or reopen the training if so desired. Communication with enquiring entities is likewise made possible, but is preferably subject to limitation. Preferably only the queries from authorised entities in authorised topic fields are allowed. The authorisation is performed (6) by way of a communication authentication storage together with a standard communication protocol function. This is a directory of those entities with which the avatar may communicate, together with conditions regarding what context the questions from the enquiring entity may relate to in order to be answered. The authorisations could be specified either by the real person themselves or by a central institution. Only authorised entities may receive information, within a clearly bounded scope: For example, an authorised medical organisation may survey the avatar, but only medical-related questions are allowed (representation of the communication between avatar and outside world in FIG. 2).

Using (7) a cryptographic storage in which access keys are administered, the avatar can preferably check what entity has what rights to receive information, and in what scope. Using this key, it is furthermore ensured that only the real person is authorised to make changes in the personal storage of the avatar.

Since the ethical avatar can be trained by the real person not only once, but said person can preferably make changes to the content of the personal storage at any time, the avatar (8) preferably comprises a storage (log storage) in which the historical course of the changes is stored (for example using blockchains or the like). Here, the avatar has (9) a clock system in order to allow chronologically absolute evaluation of the various training runs and alignment of same with the second storage device with regard to general morally relevant knowledge. In this way, the time of a particular training sequence $t_x$ can be assigned to the general state of knowledge at this exact time, as stored in the public, shared storage (see (4)). This can be of major importance for the understanding of the content of the respective training unit: For example, it can make a difference whether a real person has indicated that they feel bound to the codes of a particular community at a time $t_x$ or they do so at a time $t_{x+n}$ at which that community has reformed their codes. Both codes (the old version of $t_x$ and the reformed version of $t_{x+n}$) are stored in the second storage device (4) in a manner linked to the respective times, in the same way as the training units are stored in the personal storage (2) in a manner linked by way of the clock system to the training time. The personal attitudes of the person can thus be placed in absolute chronological order (illustration in FIG. 3).

The ethical avatar may furthermore (10) have a unit which relates to the availability, in principle, of the real person, which provides a link to a means of contact, or which makes statements relating to the contactability of the person.

In implementing the invention, there are in particular the following possibilities:

a) The real person has exactly one corresponding avatar apparatus (ethical avatar), preferably with a corresponding identification tag, at which queries can be directed by various entities. All information relating to said person is processed by means of one avatar apparatus.

b) A real person may be assigned multiple avatar apparatuses (avatar system) generated in various areas of application. Different avatars could be successfully synchronised with one individual either by way of an avatar identification number (provided by an avatar information entity), a global unique identifier (such as the patient ID or the biosample ID) or a (hashed) individual identifier (such as an image [for example, the concept of a "gravatar" has been developed—a gravatar is an image that accompanies the user from website to website and functions as an identifier (see https://de.gravatar.com)] or genetic "fingerprints" such as SNPs—single nucleotide polymorphisms—or STRs—short tandem repeats). If a person has several avatars, these avatars are preferably synchronised with one another in order that all avatars involved remain up to date with regard to the mental response characteristics, for example the attitudes and opinions, of their common real person. An alignment between the various avatars of a real person should be ensured.

Further details of specific exemplary embodiments and applications

1. Exemplary Embodiments for Big Data Analyses/Data Science

- Avatars as part of a multidirectional platform that functions as an integrating link between medical laboratories/biobanks and pharmaceutical concerns and/or scientific organisations: Medical (commercial) laboratories have access to large amounts of data relating to clinical information, diagnostic results and genetic information of patients. They have an interest in using this data by the research and industrial sectors. On the other hand, the pharmaceutical industry and scientific organisations are, in their research, reliant on obtaining data from very specific patient groups. The mediation between these sectors is very complicated when using conventional techniques, but can be made easier using a platform with at least one integrated avatar apparatus. The platform brings together the information from both sides: it analyses which patients are being tested in the laboratories and, from the queries for patent profiles from the research sector, gains an insight into which of these data/samples from the laboratories are of interest to the research sector. The platform can thus assist both sides: It advises the laboratories on which samples/data would be worth subjecting to expensive full genomic sequencing (necessary for the research sector) (because the platform knows which samples/data are of interest for the research/industrial sector), and in so doing can assist the research sector in assembling suitable cohorts. The ethical avatars of the patients assist in this preselection, inter alia because they know the moral attitudes of their real counterpart. For the use of data/samples of patients, the consent of the patients concerned is required. Ethical avatars could be used to make it easier to obtain these declarations (see below).
- Sociological research: Avatars could assist in the preselection of which persons could in principle be interested in which research topics and survey contents, or which persons would immediately lodge an objection.
  - Advantage: Fast and suitable preselection for sociological cohorts/survey groups.
- Opinion research/Big Data analyses: In order to be able to easily and quickly collate and analyse the opinions of a very large number of persons, ethical avatars can be advantageous—not only do they assist in answering specific questions from opinion research institutions, but they also assist in evaluating the suitability of their persons for a corresponding survey in the first place (by assisting with the preselection).

2. Possible Applications in a Clinical Context and in Biomedical Research

- Provision of advice in connection with questions of informed consent: The avatar learns the person's answers to the questions of various declarations of consent, and is subsequently capable of anticipating said person's attitudes to new questions and answering on their behalf. The avatar performs the role of an advisory representative of the person, which has learned to answer on behalf of its person.
  - Advantage: Establishing direct contact with the person for questions relating to their declaration(s) of consent is no longer necessary, and the privacy of the person is safeguarded whilst simultaneously taking their interests and instructions into consideration.
- Standardisation of the informed consent process: the process of obtaining declarations of consent could be standardised using an ethical avatar. The current plurality and complexity of different informed consent documents could be counteracted using such an internationally applicable, standardised instrument as the ethical avatar.
  - Advantage: The international distribution and the understanding of such documents would be simplified, and an international vocabulary and approach would be possible, greatly facilitating international cooperation.
- Dynamic patient advance directive: The avatar could perform a support function in the event of persons being unable to express themselves. Should a person be in a coma or in a similar situation in which they are not capable of speaking for themselves, a correspondingly trained ethical avatar of the person could be of great assistance to relatives or legal guardians if they could survey said avatar instead of the person with regard to said person's wishes, interests and moral attitudes.
  - Advantage: The person concerned can rely on the fact that, if they themselves are incapacitated, the ethical avatar that they have trained can anticipate decisions in their interests.
- Unpredicted future fields of research/areas of application: If the avatar is trained more broadly, it can also learn more general moral attitudes/values/principles of the corresponding person aside from specific questions of "informed consent", and anticipate answers even to questions that go beyond those of "informed consent".
  - Advantage: Rapid participation in new fields of research is made possible, with maximum use of existing cell donations.
- Stratification of cohorts for biomedical research: The avatar presented here is capable of acting on behalf of a patient/subject, without releasing their sensitive data. Here, use may be made in particular of the technique described in DE 10 2019 135 380.7 ("Verfahren and Datenverarbeitungsvorrichtung zur Bearbeitung von genetischen Daten" ["Method and data processing device for processing genetic data"], unpublished on the priority date of the present disclosure), in which searches can be performed in inaccessible data (such as the genetic information of a person) in an encrypted manner (by way of hashes) without the need for all of the information of the data to be disclosed. DE 10 2019 135 380.7 is incorporated by reference into the present disclosure, in particular with regard to the processing of genetic data. In this case, the avatar would have access to the corresponding hashes and could answer yes/no to questions posed, without having to know the encrypted information. This service would be of great advantage in particular in the assembly of patient/subject cohorts with particular common characteristics. For example, cell lines whose donors have specific, for example genetic, commonalities are often required for research objectives. In this case, the corresponding avatars could, in response to a query, confirm or else not confirm the suitability of the cell lines whose donor said avatars represent, without revealing the genetic information of their real counterpart.

The search for suitable patients/subjects could advantageously take place very quickly (answering of questions relating to specific genetic characteristics of a person), and the avatar could furthermore assist in making the preselection without disclosing the underlying sensitive data of the corresponding person.

Advantage: Safeguarding of the protection of sensitive data whilst corresponding questions are simultaneously answered, and rapid stratification of cohorts for the research, which has hitherto been possible only with great effort and great expenditure of time.

Synthetic biology: In the future, it may become possible for synthetic biological units, cells or organoids to be developed from genetic information alone—in this case, too, the ethical avatar would be conceivable as a representative entity between real persons (to whom the genetic information pertains) and research organisations. The avatar could, on behalf of the person, express consent or prohibitions with regard to what may or may not be created synthetically.

Advantage: In new fields of research and areas of application, the person is represented whilst protection of their identity is safeguarded, and questions can be answered quickly and reliably by the advisory avatar on behalf of the person concerned.

3. Use in the Context of Application of Law

Assistance in assessing the accountability of a person: The question of whether a person is correspondingly accountable in respect of a law is dependent inter alia on how consistent their opinions are and whether their opinions have changed very often, and in a contradictory manner, in recent time. All of this can be implemented by way of an avatar which knows not only the present opinions of a person but also the "course" of their opinions and can examine the logical and, if appropriate, contradictory relationships between different opinions. The avatar could be an aid for the justice system and psychological experts to assess the mental state of a person. This could also be relevant for psychological assessment in a medical context: Inconsistencies within opinions could be an indication of increasing confusion/dementia of the person.

Advantage: Experts would not only be provided with the present state of a person for assessment but could also consider the course of their opinions over time, or the dynamics of their opinions over time.

4. Embodiments for the Control of Technical Equipment

Use for technical equipment: Avatars could assist technical equipment in implementing the desires and interests of their users: for example by controlling filter systems in various Internet search engines such that only the desired content is displayed to the person, and other content is excluded; avatars could also perform custodial functions for minors by ensuring that no content unsuitable for minors is displayed to the minors.

Facilitation of targeted use of technical equipment in a manner suited to the desires/interests and moral attitudes of the user Moral implementation in self-driving cars: In the search for suitable moral systems for self-driving cars, common-sense solutions have hitherto been sought (implementing the average moral attitude), but it would also be possible for any driver to implement their own moral attitude in their self-driving vehicle, specifically with the aid of their ethical avatar. The avatar then functions as an individual conscience of the vehicle, like the human driver in non-self-driving cars.

Advantage: The driver does not have to submit to the dictum of average moral attitudes but can (self-evidently within the scope of what is legal) implement their personal ethical values in a road traffic context (as they would when driving manually).

5. Other Embodiments

Administration/safeguarding of the access key to pseudo-anonymised personal data: To protect the personal rights and the privacy of persons, their data are, in many areas of application, protected by encryption. Here, the administration of this key is of great importance. Forgetfulness or carelessness of the persons can result in loss of this access key. An ethical avatar could assist here in safeguarding this key for the corresponding person and protecting said key against access by unauthorised parties.

Advantage: The responsibility of the person is assisted by the aid of the ethical avatar, the key would be professionally administered and safeguarded, and loss is made unlikely.

Monitoring of data protection: The avatar constitutes a link in the communication between persons and (medical) organisations and/or research institutions.

Advantage: Direct contact with the person is not necessary, and their identity remains protected whilst simultaneously allowing the maximum opportunity for participation in questions relating to them and their interests. Furthermore, the avatar can answer questions without having to reveal sensitive data (see above).

Provision of additional moral-philosophical competencies: The ethical avatar not only has access to the learned values/moral attitudes/principles of the physical person but also has further-reaching general moral-philosophical knowledge (in a separate storage shared with other avatars). During the training conversation with the person, the ethical avatar can use this knowledge to sensitise said person to further-reaching moral questions and survey said person more intelligently. In this way, the avatar would be more than a purely receiving entity that merely learns the attitudes of the person. It would furthermore be an understanding counterpart with its own moral competencies, which it however uses only during the process of training by the person. After the training, when answering questions regarding the moral attitude of its real person, said avatar would adhere to the statements made by the person without accessing its own general moral-philosophical knowledge.

Advantage: Many persons are not initially aware of the significances of their moral attitudes—moral competencies of the ethical avatar allow the persons to be intelligently surveyed during the training conversation without undermining their decision-making autonomy. Furthermore, interested persons can in this way (by conversation with their avatar) be motivated to contemplate response characteristics, such as moral response characteristics, and train themselves in their own moral judgements.

The features of the invention disclosed in the description above, in the drawings and in the claims may be of importance both individually and in combination or sub-combination for realising the invention in its various embodiments.

What is claimed is:

1. An avatar apparatus that is adapted to represent a person and to process personal data of the person, comprising:

an AI processor device that is adapted for machine learning of individual mental response characteristics of the person by way of data training, wherein the AI processor device is configured to generate semantic answers in response to questions in a manner dependent on the mental response characteristics, a first storage device that is coupled to the AI processor device and is adapted to store the mental response characteristics of the person, wherein the first storage device is set up to store individual additional data on which the mental response characteristics are dependent, a second storage device that is set up to store general additional data that represent knowledge relevant to the mental response characteristics, wherein the second storage device is coupled to an update device by means of which the general additional data can be updated and the second storage device is adapted to be used during the data training of the avatar device only, an input device that is coupled to the AI processor device and is adapted to at least one of interacting with the person and receiving questions relating to the person, and an output device that is configured to output signals that represent the answers generated by the AI processor device.

2. The avatar apparatus according to claim 1, wherein the AI processor device is adapted for the machine learning of the individual mental response characteristics, which include at least one of moral attitudes, opinions, values, interests and ethical principles.

3. The avatar apparatus according to claim 1, wherein the first storage device is configured to store the mental response characteristics in the form of catalogues of at least one of rules, micro-contracts and blockchains.

4. The avatar apparatus according to claim 1, wherein the AI processor device being adapted to understand and use ethically relevant expressions.

5. The avatar apparatus according to claim 1, wherein the input device comprises a communication channel that is adapted for communication between the avatar apparatus and the person.

6. The avatar apparatus according to claim 1, wherein the input device is provided with an authorizing device that is configured to restrict the receipt of questions relating to the person to at least one of predetermined authorized entities and predetermined allowable contents.

7. The avatar apparatus according to claim 6, wherein the authorizing device comprises a communication authentication storage and a standard communication protocol function.

8. The avatar apparatus according to claim 1, furthermore comprising a cryptographic storage that is adapted to store access keys.

9. The avatar apparatus according to claim 1, furthermore comprising a log storage that is adapted to store a course of changes to the contents of at least one of the first and second storage devices.

10. The avatar apparatus according to claim 1, furthermore comprising a timer device that is adapted to provide a timescale for the functions of the avatar apparatus.

11. The avatar apparatus according to claim 1, furthermore comprising a communication device that is adapted to at least one of establishing contact and communicating with the person.

12. An avatar system comprising multiple avatar apparatuses according to claim 1, wherein each avatar apparatus is adapted to a different application.

13. A method of using an avatar apparatus according to claim 1, comprising at least one of the following forming a multidirectional platform for placing at least one of medical laboratories and biobanks in connection with at least one of industrial companies and scientific research organizations, forming a platform for at least one of social research, opinion research and Big Data analysis, forming a platform for providing patient declarations, forming a data protection platform, generating a patient advance directive, providing input information for a synthetic biological procedure, and controlling technical systems.

14. An avatar method for operating an avatar apparatus of a person according to claim 1, comprising:

receiving at least one question relating to the person, processing the question using the AI processor device, and outputting a semantic answer to the at least one question.

15. The avatar method according to claim 14, wherein the processing of the question using the AI processor device is performed in a manner dependent on at least one of moral attitudes, opinions, values, interests and ethical principles of the person.

16. The avatar method according to claim 14, wherein the mental response characteristics are stored in the form of catalogues of at least one of rules, micro-contracts and blockchains.

17. The avatar method according to claim 14, wherein individual additional data are stored, on which the mental response characteristics are dependent.

18. The avatar method according to claim 14, wherein the AI processor device understands and uses ethically relevant expressions.

19. The avatar method according to claims 14, furthermore comprising storing of general additional data that represent knowledge relevant to the mental response characteristics.

20. The avatar method according to claim 19, wherein the general additional data are updated at predetermined times.

21. The avatar method according to claim 14, furthermore comprising a communication between the avatar apparatus and the person.

22. The avatar method according to claim 14, wherein the receipt of questions relating to the person is restricted by means of an authorizing device to at least one of predetermined authorized entities and predetermined allowable contents.

23. The avatar method according to claims 14, furthermore comprising storing of access keys in a cryptographic storage.

24. The avatar method according to claim 14, furthermore comprising storing of a course of changes to the contents of at least one of the first and second storage devices.

25. The avatar method according to claim 14, furthermore comprising providing of a timescale for the functions of the avatar apparatus.

26. The avatar method according to claim 14, furthermore comprising an establishment of at least one of contact and communication with the person.

* * * * *